United States Patent
McCann et al.

(10) Patent No.: US 7,918,978 B2
(45) Date of Patent: Apr. 5, 2011

(54) PHOTOFORMED SILICONE SENSOR MEMBRANE

(75) Inventors: Margot Leanne McCann, Ottawa (CA); Sandra Kay Shaw, Ottawa (CA); Karl John Anthony Underwood, Ottawa (CA); Harvey Eric Rabe, Ashton (CA)

(73) Assignee: I-STAT Corporation, East Windsor, NJ (US)

( * ) Notice: Subject to any disclaimer, the term of this patent is extended or adjusted under 35 U.S.C. 154(b) by 1188 days.

(21) Appl. No.: 11/484,579

(22) Filed: Jul. 12, 2006

(65) Prior Publication Data
US 2007/0015977 A1 Jan. 18, 2007

Related U.S. Application Data

(60) Provisional application No. 60/698,927, filed on Jul. 14, 2005.

(51) Int. Cl.
*G01N 27/40* (2006.01)
*C08J 7/18* (2006.01)

(52) U.S. Cl. .................. 204/435; 204/403.01; 204/432; 427/510; 427/515; 522/91

(58) Field of Classification Search .................. 204/400, 204/432, 435, 403.01; 427/510, 515; 522/91
See application file for complete search history.

(56) References Cited

U.S. PATENT DOCUMENTS

| | | | |
|---|---|---|---|
| 4,933,048 A | 6/1990 | Lauks | |
| 4,933,087 A | 6/1990 | Markham, Jr. et al. | |
| 5,112,455 A | 5/1992 | Cozzette et al. | |
| 5,200,051 A | 4/1993 | Cozzette et al. | |
| 5,514,253 A | 5/1996 | Davis et al. | |
| 5,554,339 A | 9/1996 | Cozzette et al. | |
| 6,030,827 A | 2/2000 | Davis et al. | |
| 6,413,393 B1 | 7/2002 | Van Antwerp et al. | |
| 6,737,117 B2 | 5/2004 | Boisvert et al. | |
| 6,770,726 B1 | 8/2004 | Arkles et al. | |
| 2002/0179448 A1 * | 12/2002 | Lauks | 204/600 |
| 2004/0074785 A1 | 4/2004 | Holker et al. | |
| 2004/0231984 A1 | 11/2004 | Lauks et al. | |

OTHER PUBLICATIONS

International Search Report (2 pages), issued for the corresponding application PCT/US2006/026939, mailed Sep. 13, 2007.
Written Opinion (5 pages), issued for the corresponding application PCT/US2006/026939, mailed Sep. 13, 2007.
Extended European Search Report for European Application No. 06786926.
Barry Arkles et al., "High Density Silicon Dioxide Coatings By UV And Thermal Processing", Silicones in Coatings III, Mar. 28-30, 2000, Barcelona, Spain.

* cited by examiner

*Primary Examiner* — Kaj K Olsen
(74) *Attorney, Agent, or Firm* — Katten Muchin Rosenman LLP

(57) ABSTRACT

A sensing device includes a sensing surface, and a matrix overlaying the sensing surface. The sensing device includes a photoformed membrane overlaying at least a portion of the matrix. The photoformed membrane includes a directly photoformed organosiloxane polymer that is substantially permeable to gaseous molecules and substantially impermeable to non-gaseous molecules and ions.

30 Claims, 8 Drawing Sheets

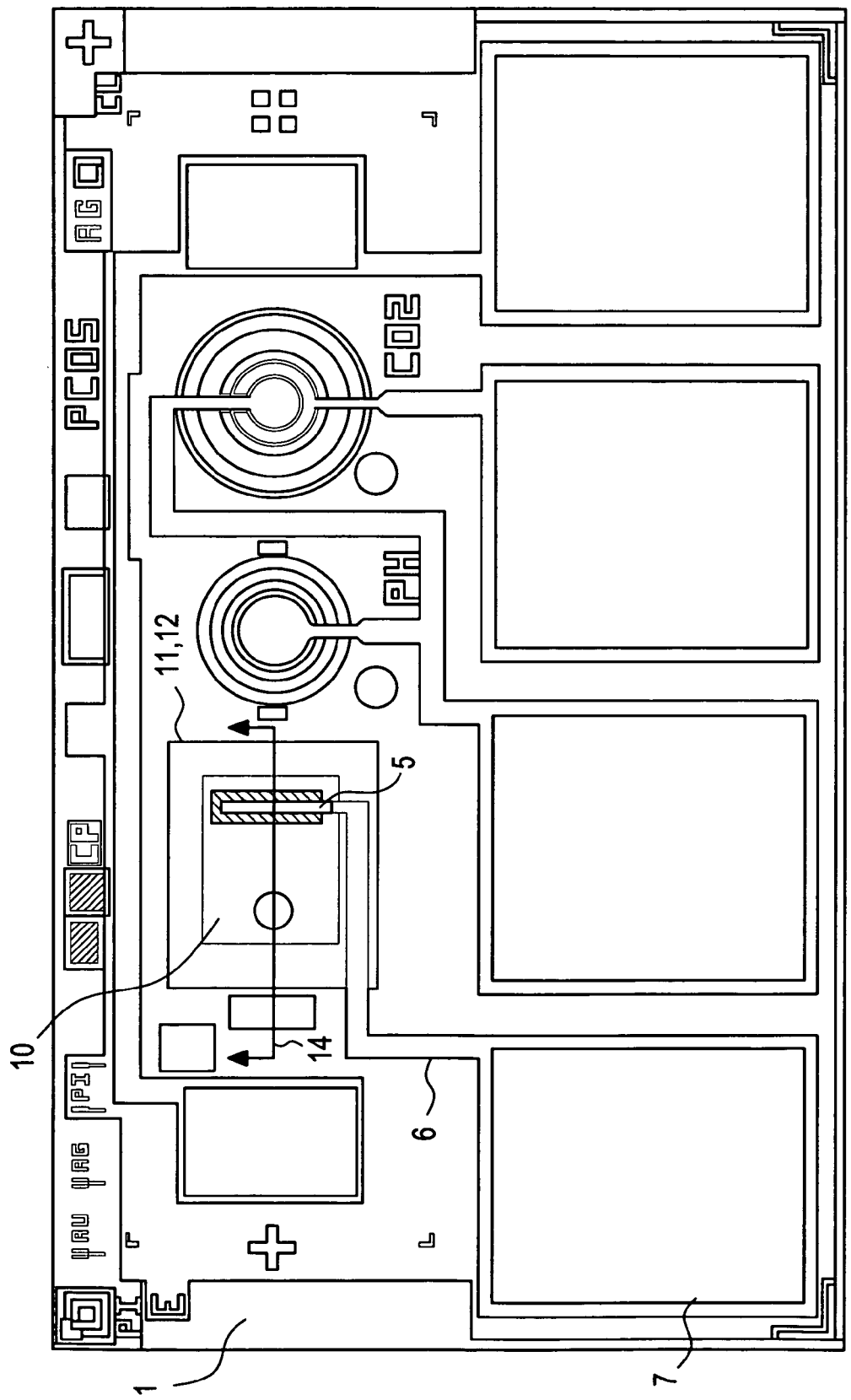

Minimized Liquid Junction Potential as a function of Reference Sensor Potential in Calibrant Solution
Junction Potential as Function of Salt Bridge [KCl]

Glucose Test Data with Dow Corning WL-7154 (new process) compared to Block Copolymer of DMPS-Polycarbonate (conventional process)

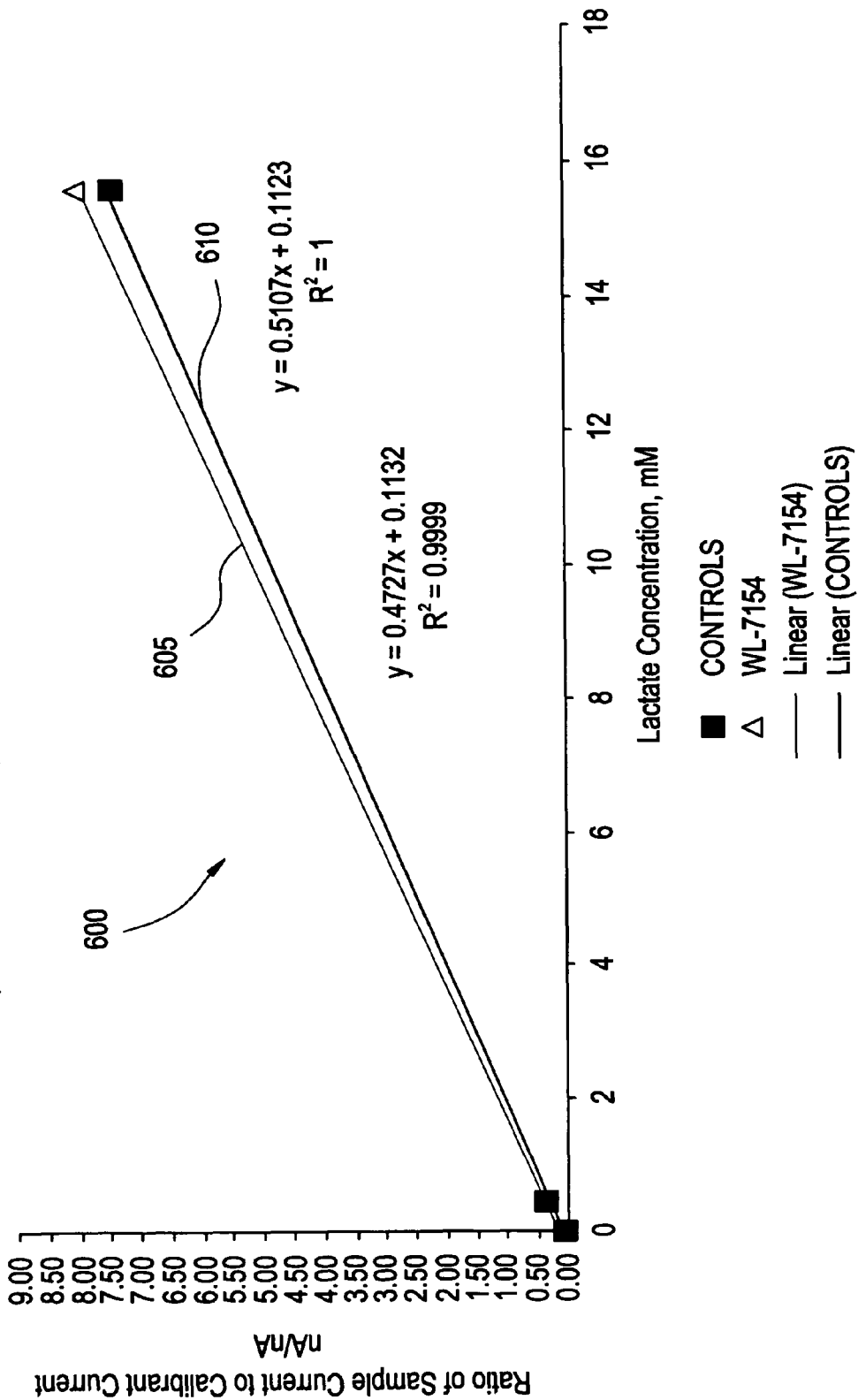

PHOTOFORMED SILICONE SENSOR MEMBRANE

This application claims priority under 35 U.S.C. §119(e) to U.S. Provisional Application No. 60/698,927, filed on Jul. 14, 2005, the entire contents of which are hereby incorporated by reference herein.

BACKGROUND

1. Field of the Invention

The present invention relates to sensor devices and methods of manufacture thereof. More particularly, the present invention relates to a sensing device and method of manufacture based on photo-formed silicone membranes that are substantially permeable to gaseous molecules, but substantially impermeable to non-gaseous molecules and ions.

2. Background Information

Microfabricated membranes, based on silicone materials, that are substantially permeable to gaseous molecules, but substantially impermeable to non-gaseous molecules and ions, are known. However, the silicone materials that have been used successfully are not directly photoformable. Therefore, indirect means have been used to achieve photo-patterning at specific locations on a surface.

For example, U.S. Pat. No. 5,200,051 teaches an analyte attenuation layer used in an amperometric sensor that contains a siloxane/non-siloxane copolymer. In one embodiment, a dimethylsiloxane-bisphenol A carbonate copolymer, dissolved in a solvent, is spin-coated onto a wafer and then coated with a gelatin photoresist layer. Such a photoresist layer is then patterned by selective exposure to ultraviolet (UV) radiation though a photomask and developed. Such a process leaves photo-cured resist material protecting the underlying copolymer, while the unexposed photoresist layer and the underlying copolymer are removed with a wet etching agent, e.g., tetramethylammonium hydroxide in methanol.

Such an indirect method can enable the copolymer to be photo-patterned, even though it is not itself a photoactive material. However, while the resulting copolymer membrane exhibits metabolite (e.g., glucose) transport attenuation, and is freely permeable to oxygen, the process of manufacture is complex, which lowers yield and raises the cost of the finished product.

Additionally, U.S. Pat. No. 6,030,827 teaches sensor structures for measuring glucose and the like, with microfabricated apertures in a siloxane/non-siloxane copolymer, in which glucose can only enter a matrix through one or more patterned apertures, whereas oxygen passes directly through the copolymer. U.S. Pat. No. 5,514,253 teaches oxygen and carbon dioxide sensor structures with patterned siloxane/non-siloxane copolymer layers.

Furthermore, U.S. Pat. No. 4,933,048 teaches a reference electrode structure that comprises a silver-silver chloride electrode in contact with a matrix containing chloride ions, and an encapsulating layer that is permeable to water vapor, but impermeable to ions. The encapsulating layer can be formed from polyvinyl chloride, polytetrafluoroethylene and silicone rubber. A distal salt bridge exists in the layer to permit exchange of ions with a fluid in contact with the device.

U.S. Pat. No. 6,737,117 teaches a dielectric protective coating material for semiconductor devices in which the coating comprises a siloxane-based resin having a relatively low dielectric constant. The coating material is based on a hydrosilsesquioxane resin that is cured by exposure to ultraviolet light to provide a passivating or scratch-resistant dielectric coat.

Gelest Inc. of Morrisville, Pa. provides a range of ultraviolet cured acrylate-modified silicone elastomers (e.g., ZIPCONE™ U Series), demonstrated to be suitable for cladding of optical components and as elastomeric shields. In addition, U.S. Pat. No. 6,770,726 teaches photo- and thermally-labile siloxane polymers that undergo transformation to $SiO_2$-rich films by elimination of beta-substituted alkyl groups.

Based on the foregoing, a need exists for sensing devices made by simple and reliable manufacturing processes for gas permeable membranes formed in a single convenient step that are impermeable to ions and metabolites.

SUMMARY OF THE INVENTION

A photoformed silicone sensor membrane and method of manufacture thereof are disclosed.

An object of the present invention is to provide a gas-permeable membrane that is impermeable to non-gaseous molecules and ions, comprising a photoformed organosiloxane polymer membrane.

Another object of the present invention is to provide a gas-permeable membrane that is impermeable to non-gaseous molecules and ions, comprising a photoformed membrane based on silsesquioxane polymers.

A further object of the present invention is to provide a method of making a photoformed gas-permeable membrane that is substantially impermeable to non-gaseous molecules and ions, comprising: applying an organosiloxane polymer to a surface to form a layer, applying ultraviolet (UV) radiation to at least a portion of the layer to cause the polymer to form an adhered membrane on the surface, and then exposing the layer to a developer to selectively remove polymer not exposed to radiation, while leaving the adhered membrane undisturbed.

Another object of the present invention is to provide a method of making a photoformed gas-permeable membrane that is substantially impermeable to non-gaseous molecules and ions, comprising: applying a silsesquioxane polymer to a surface to form a layer, applying UV radiation to at least a portion of the layer to cause the polymer to form an adhered membrane on the surface, and then exposing the layer to a developer to selectively remove polymer not exposed to radiation, i.e., a photolithographic process.

An additional object of the present invention is to provide a method of making a photoformed gas-permeable membrane that is substantially impermeable to non-gaseous molecules and ions, comprising: microdispensing a desired volume of an organosiloxane polymer onto a surface to form a layer, and then applying UV radiation to the layer to cause the polymer to form an adhered membrane on the surface.

A further object of the present invention is to provide a method of making a photoformed gas-permeable membrane that is substantially impermeable to non-gaseous molecules and ions, comprising: microdispensing a desired volume of a silsesquioxane polymer onto a surface to form a layer, and then applying UV radiation to the layer to cause the polymer to form an adhered membrane on the surface.

An object of the present invention is to provide a sensing device, comprising: a light-cured silicone membrane that is substantially permeable to gaseous molecules and substantially impermeable to non-gaseous molecules and ions.

An additional object of the present invention is to provide a sensing device, comprising: a sensing surface, a matrix overlaying the sensing surface, and a photoformed membrane overlaying at least a portion of the matrix, where the photoformed membrane is made from a photo-labile organosiloxane polymer, and where the membrane is substantially permeable to gaseous molecules and substantially impermeable to non-gaseous molecules and ions.

Another object of the present invention is to provide a reference electrode, comprising: a silver-silver chloride sensing surface, a matrix containing chloride ions overlaying the sensing surface, and a photoformed silicone membrane overlaying at least a portion of the matrix that is substantially permeable to water vapor and substantially impermeable to ions, but has at least one orifice to permit exchange of chloride ions.

A further object of the present invention is to provide an oxygen sensing device, comprising: a noble metal surface, a matrix overlaying the sensing surface, and a photoformed silicone membrane overlaying at least a portion of the matrix, wherein the membrane is substantially permeable to oxygen molecules and substantially impermeable to non-gaseous molecules and ions.

Another object of the invention is to provide a carbon dioxide sensing device, comprising: a pH sensing surface, a matrix which contains carbonic anhydrase and quinhydrone overlaying the sensing surface, and a photo-cured microdispensed silicone membrane overlaying the matrix, wherein the membrane is substantially permeable to carbon dioxide molecules and substantially impermeable to non-gaseous molecules and ions.

More particularly, a sensing device and method of manufacture based on photo-formed silicone membranes that are substantially permeable to gaseous molecules, but substantially impermeable to non-gaseous molecules and ions, are disclosed. In accordance with exemplary embodiments, according to a first aspect of the present invention, a sensing device includes a sensing surface, and a matrix overlaying the sensing surface. The sensing device includes a photoformed membrane overlaying at least a portion of the matrix. The photoformed membrane comprises a directly photoformed organosiloxane polymer that is substantially permeable to gaseous molecules and substantially impermeable to non-gaseous molecules and ions.

According to the first aspect, the organosiloxane polymer can comprise a silsesquioxane polymer. Alternatively, the organosiloxane polymer can comprise a beta-substituted silsesquioxane polymer. The organosiloxane polymer can comprise a hydrosilsesquioxane polymer or the like. A bound moiety can be displaced by exposure to light to form the photoformed membrane. For example, the light can comprise one or more wavelengths falling in the range of about 200 nanometers to about 400 nanometers. The organosiloxane polymer can be crosslinked by the action of a photoinitiator. The photoformed membrane can substantially or completely enclose the matrix. The photoformed membrane can also be patterned to provide a substantially fixed geometric relationship with the matrix. Furthermore, the photoformed membrane can be patterned to provide a substantially fixed geometric relationship with the matrix and the sensing surface.

According to the first aspect, the sensing device can be configured to detect oxygen, carbon dioxide, or water vapor. The sensing device can be configured to detect glucose, lactate, creatinine, ascorbate, urate, and/or bilirubin. The sensing device can be configured to detect ions selected from the group consisting of chloride, potassium, sodium, calcium, proton and hydroxide. The sensing surface can be selected from the group consisting of a metal electrode, a non-metal electrode and an optical wave guide. Alternatively, the sensing surface can be selected from the group consisting of platinum, gold, iridium, silver, silver halide, silver chloride and carbon. The sensing surface can be adapted for potentiometry or amperometry. The matrix can be selected from the group consisting of polyvinyl alcohol, photoformed polyvinyl alcohol, gelatin, photoformed gelatin and nitrocellulose. The matrix can include a bioactive molecule. For example, the matrix can include a bioactive molecule selected from the group consisting of glucose oxidase, lactate oxidase, bilirubin oxidase, ascorbate oxidase, carbonic anhydrase, sarcosine oxidase, creatinase and creatininase. The matrix can also include a redox species. Furthermore, the matrix can include a redox species selected form the group the group consisting of quinhydrone, a ferrocene, ferrocyanide and ferricyanide. The matrix can include an ion species. According to an alternative exemplary embodiment of the first aspect, the matrix can include chloride ions.

According to a second aspect of the present invention, a reference electrode includes a silver-silver chloride sensing surface, and a matrix containing chloride ions overlaying the sensing surface. The reference electrode includes a directly photoformed membrane overlaying at least a portion of the matrix. The photoformed membrane comprises an organosiloxane polymer that is substantially permeable to water vapor and substantially impermeable to ions. The photoformed membrane comprises at least one orifice configured to permit exchange of ions.

According to the second aspect, the organosiloxane polymer can comprise a silsesquioxane polymer. Alternatively, the organosiloxane polymer can comprise a beta-substituted silsesquioxane polymer. The organosiloxane polymer can comprise a hydrosilsesquioxane polymer or the like. A bound moiety can be displaced by exposure to light to form the photoformed membrane. For example, the light can comprise one or more wavelengths falling in the range of about 200 nanometers to about 400 nanometers. The organosiloxane polymer can be crosslinked by the action of a photoinitiator. The photoformed membrane can substantially or completely enclose the matrix. The photoformed membrane can be patterned to provide a fixed or substantially fixed geometric relationship with the matrix. Furthermore, the photoformed membrane can be patterned to provide a fixed or substantially fixed geometric relationship with the matrix and the sensing surface.

According to a third aspect of the present invention, an oxygen sensing device includes a noble metal sensing surface, and a matrix overlaying the sensing surface. The oxygen sensing device includes a directly photoformed membrane overlaying at least a portion of the matrix. The photoformed membrane comprises an organosiloxane polymer that is substantially permeable to oxygen molecules and substantially impermeable to non-gaseous molecules and ions.

According to the third aspect, the organosiloxane polymer can comprise a silsesquioxane polymer. Alternatively, the organosiloxane polymer can comprise a beta-substituted silsesquioxane polymer. The organosiloxane polymer can comprise a hydrosilsesquioxane polymer or the like. A bound moiety can be displaced by exposure to light to form the photoformed membrane. For example, the light can comprise one or more wavelengths falling in the range of about 200 nanometers to about 400 nanometers. The organosiloxane polymer can be crosslinked by the action of a photoinitiator. The photoformed membrane can substantially or completely enclose the matrix. The photoformed membrane can be patterned to provide a fixed or substantially fixed geometric relationship with the matrix. Furthermore, the photoformed membrane can be patterned to provide a fixed or substantially fixed geometric relationship with the matrix and the sensing surface.

According to a fourth aspect of the present invention, a carbon dioxide sensing device includes a sensing surface. The carbon dioxide sensing device includes a matrix comprising carbonic anhydrase and quinhydrone overlaying at least a portion of the sensing surface. The carbon dioxide sensing device includes a directly photoformed membrane overlaying the matrix. The photoformed membrane comprises an organosiloxane polymer that is substantially permeable to carbon dioxide molecules and substantially impermeable to non-gaseous molecules and ions.

According to the fourth aspect, the organosiloxane polymer can comprise a silsesquioxane polymer. Alternatively, the organosiloxane polymer can comprise a beta-substituted silsesquioxane polymer. The organosiloxane polymer can comprise a hydrosilsesquioxane polymer or the like. A bound moiety can be displaced by exposure to light to form the photoformed membrane. For example, the light can comprise one or more wavelengths falling in the range of about 200 nanometers to about 400 nanometers. The organosiloxane polymer can be crosslinked by the action of a photoinitiator. The photoformed membrane can substantially or completely enclose the matrix. The photoformed membrane can be patterned to provide a fixed or substantially fixed geometric relationship with the matrix. Furthermore, the photoformed membrane can be patterned to provide a fixed or substantially fixed geometric relationship with the matrix and the sensing surface.

According to a fifth aspect of the present invention, a photoformed gas-permeable membrane that is substantially impermeable to non-gaseous molecules and ions includes an organosiloxane polymer from which a bound moiety has been displaced by exposure to light to form the membrane.

According to the fifth aspect, the light can comprise one or more wavelengths falling in the range of about 200 nanometers to about 400 nanometers. The membrane can be in contact with a matrix layer. The membrane can substantially or completely enclose the matrix. The membrane can be patterned to provide a fixed or substantially fixed geometric relationship with the matrix. The organosiloxane polymer can comprise a silsesquioxane polymer. Alternatively, the organosiloxane polymer can comprise a beta-substituted silsesquioxane polymer. The organosiloxane polymer can comprise a hydrosilsesquioxane polymer or the like.

According to a sixth aspect of the present invention, a photoformed gas-permeable membrane that is substantially impermeable to non-gaseous molecules and ions, wherein the membrane is formed from a silsesquioxane polymer by direct exposure to light.

According to the sixth aspect, the light can comprise one or more wavelengths falling in the range of about 200 nanometers to about 400 nanometers. The membrane can be in contact with a matrix layer. The membrane can substantially or completely enclose the matrix. The membrane can be patterned to provide a fixed or substantially fixed geometric relationship with the matrix.

According to a seventh aspect of the present invention, a method of making a photoformed, gas-permeable membrane that is substantially impermeable to non-gaseous molecules and ions includes the steps of: a.) applying an organosiloxane polymer having a bound labile moiety to a surface to form a layer; b.) applying UV radiation to at least a portion of the layer to remove the labile moiety and to cause the organosiloxane polymer to form an adhered membrane on the surface; and c.) exposing the layer to a developer to selectively remove the organosiloxane polymer not exposed to the UV radiation.

According to the seventh aspect, the organosiloxane polymer can comprise a silsesquioxane polymer. Alternatively, the organosiloxane polymer can comprise a beta-substituted silsesquioxane polymer. The organosiloxane polymer can comprise a hydrosilsesquioxane polymer or the like.

According to an eighth aspect of the present invention, a method of making a photoformed, gas-permeable membrane that is substantially impermeable to non-gaseous molecules and ions includes the steps of: a.) applying a silsesquioxane polymer to a surface to form a layer; b.) applying UV radiation to at least a portion of the layer to cause the silsesquioxane polymer to form an adhered membrane on the surface; and c.) exposing the layer to a developer to selectively remove the silsesquioxane polymer not exposed to the UV radiation.

According to a ninth aspect of the present invention, a method of making a photoformed, gas-permeable membrane that is substantially impermeable to non-gaseous molecules and ions includes the steps of: a.) microdispensing a desired volume of an organosiloxane polymer with a bound labile moiety to a surface to form a layer; and b.) applying UV radiation to the layer to remove the moiety and to cause the organosiloxane polymer to form an adhered membrane on the surface.

According to a tenth aspect of the present invention, a method of making a photoformed, gas-permeable membrane that is substantially impermeable to non-gaseous molecules and ions includes the steps of: a.) microdispensing a desired volume of a silsesquioxane polymer to a surface to form a layer; and b.) applying UV radiation to the layer to cause the silsesquioxane polymer to form an adhered membrane on the surface.

According to an eleventh aspect of the present invention, a method of establishing a patterned layer over a surface includes the steps of: a.) applying to a surface a layer comprising a homogenous mixture of an organosilicone polymer bearing labile groups and an effective amount of a photoinitiator; b.) exposing selected portions of the layer to UV light under conditions sufficient to polymerize the exposed portions of the layer; and c.) removing unexposed portions of the layer from the surface to provide a patterned layer over the surface.

BRIEF DESCRIPTION OF THE DRAWINGS

Other objects and advantages of the present invention will become apparent to those skilled in the art upon reading the following detailed description of preferred embodiments, in conjunction with the accompanying drawings, wherein like reference numerals have been used to designate like elements, and wherein:

FIGS. 1(a) and 1(b) are diagrams illustrating plan views of the conventional and the present sensing chip, respectively, incorporating a reference sensor, in accordance with an exemplary embodiment of the present invention.

FIG. 6 is a graph illustrating the linear response of lactate sensors made with the inventive process and the conventional process, respectively, as measured against the expected gravimetric concentration of lactate, in accordance with an exemplary embodiment of the present invention.

DETAILED DESCRIPTION OF THE PREFERRED EMBODIMENTS

Figure 1B:
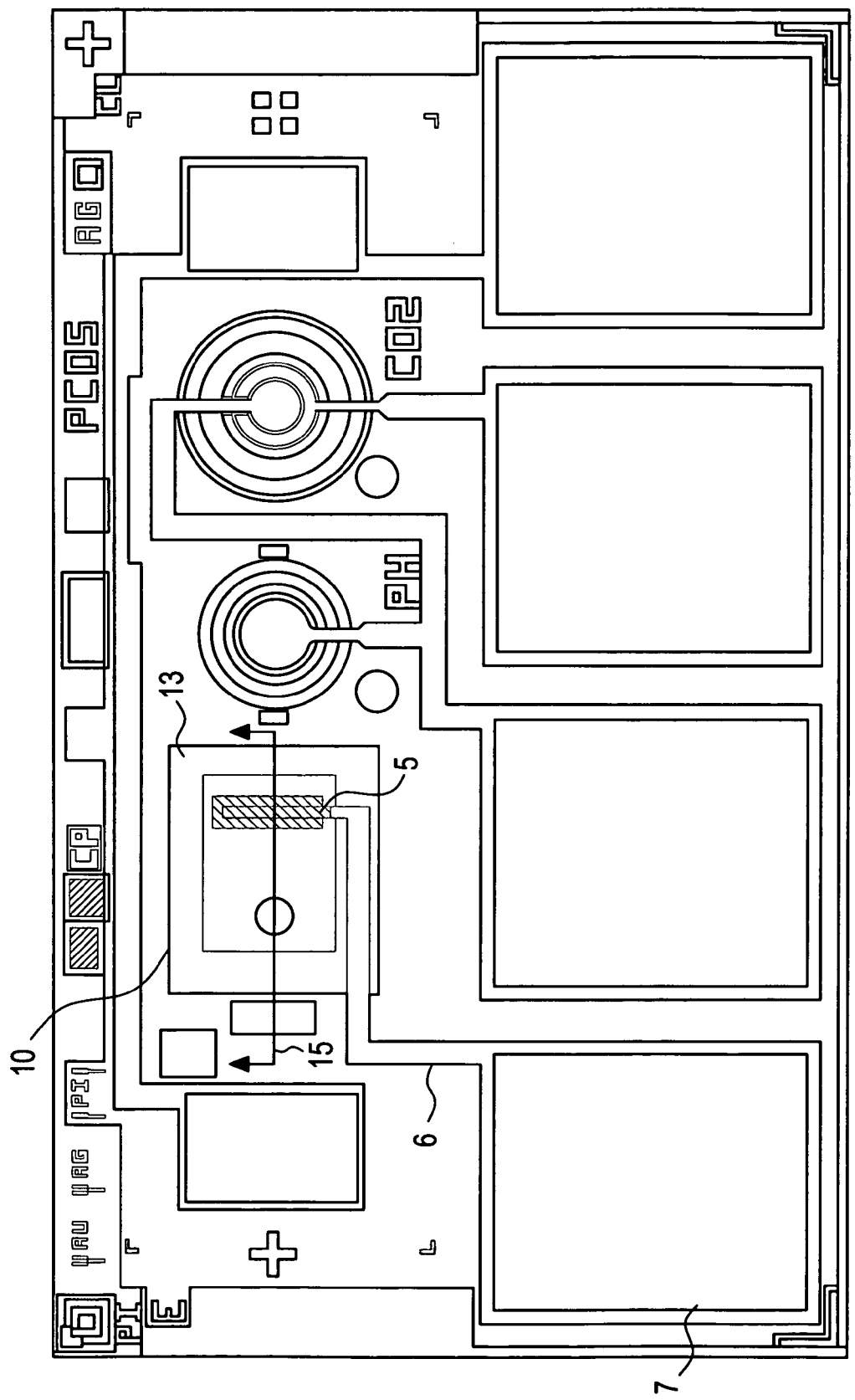

Exemplary embodiments of the present invention are directed to a sensing device and method of manufacture based on photo-formed silicone membranes that are substantially permeable to gaseous molecules, but substantially impermeable to non-gaseous molecules and ions. More particularly, the present invention relates to sensing devices having light-cured silicone membranes useful for detecting the presence or concentration of various molecules in a sample. The devices can be used as sensors for laboratory auto-analyzers and in single-use disposable cartridges for conducting real-time, or near real-time, assays of analytes. According to an exemplary embodiment, the present invention relates to analyte sensors for making determinations in liquid samples, including, for example, blood, of analytes, such as, for example, glucose, lactate, creatinine, oxygen partial pressure, carbon dioxide partial pressure and the like. Exemplary embodiments of the present invention can also be used in reference sensors based on silver-silver chloride and other like electrochemical couples in conjunction with the aforesaid analyte sensors, to provide a half-cell potential against which the analyte sensor potential can be measured. Such reference sensors can also be used in conjunction with amperometric measurements.

Conventional gas permeable materials that are not directly photoformable, but which have found utility in sensor manufacturing, include, for example, block copolymers of dimethyl polysiloxane (DMPS) and polycarbonate. For example, the copolymers are prepared to about 6% solids in a solution of methylene chloride and chlorobenzene.

In order to pattern a layer of such a copolymer, a coating of photo-patternable material (e.g., dichromated gelatin or stilbizonium treated polyvinyl alcohol, optionally blended with bovine serum albumin to aid adhesion of PVA to an underlying surface) is deposited over the top of the copolymer membrane layer. Such a second layer is then patterned to form a protective cap layer using photolithography, and then a wet-etch process is used to remove the copolymer from unprotected areas. Siloxane copolymers of this type are known to have good gas permeability and mechanical properties (e.g., flexibility) and are substantially impermeable to non-gaseous molecules and ions.

It is particularly desirable to avoid the need for such indirect patterning of the gas permeable membrane, and to have the material from which the membrane is formed be directly photoformable. This is particularly advantageous for the production of microfabricated sensors because it permits a simplified manufacturing processes, better reliability, lower cost, and improved fidelity of microstructure dimensions.

The important properties of a photoformed gas-permeable membrane according to exemplary embodiments of the present invention relate to its suitability for microfabrication. Preferably, the material has high permeability to water vapor, to oxygen, to carbon dioxide and the like, but is substantially impermeable to neutral molecules (e.g., having a molecular weight above about 120 Daltons) and to ions (e.g., those which generally exist in hydrated form, such as, for example, $[X,H_2O_{(n)}]^-$). According to an exemplary embodiment, the membrane can also be sufficiently flexible to allow for swelling upon rehydration of any of the other layers it is in contact with, such as, for example, an underlying gel matrix layer. Such swelling should preferably occur without cracking or deformation of the membrane.

It is also desirable that the manufacturing process have a degree of simplicity and robustness suitable for microfabrication, including, for example, consistent adhesion to surfaces underneath or above, and patterning to a consistent thickness and feature size, typically from about 0.1 to about 10 microns in thickness and features of about 20 μm width and greater. The resulting photoformed membranes can also exhibit pattern integrity in that the resulting pattern survives downstream processes, such as, for example, silicon wafer dicing (e.g., the absence of delamination) or the like. Mixtures of the photoformable material can also exhibit minimal radial thickness variations when the material has been spin-coated onto a planar surface (e.g., a silicon wafer).

Where the membrane is used as a gas-permeable membrane in conjunction with a microfabricated sensor, the membrane can also have the following properties, including, but not limited to: i.) the membrane should not contaminate the equipment used for patterning; ii.) the membrane should have stability at room temperature and be stable for several weeks, although the membrane can have such stability for any suitable time period; and iii.) the membrane should offer several months of storage under a specified set of conditions, although such storage can be for any appropriate length of time. The membrane should also provide suitable sensor behavior, including, for example, the raw signal increasing substantially linearly with increasing concentration of the sensed analyte over the entire or substantially entire—or a large portion of—reportable range of the analyte. The membrane should demonstrate good discrimination, permitting substantially free passage of gaseous molecules, while substantially blocking passage of non-gaseous molecules and ions.

Surprisingly, the inventors of the present invention have found that these and other desirable properties can be achieved in mixtures of photoformable materials and their resulting photoformed membranes that were originally contemplated to form photo-cured dielectric coatings for passivating electronic devices, and for providing scratch-resistant coatings for circuit boards, optical components, windscreens, computer screens and the like. Such mixtures, including, for example, UV-curable polysiloxanes, had not been patterned or subjected to a photolithographic process prior to the present invention. Furthermore, the success of these conventional applications of such photo-cured polysiloxanes did not contemplate or require the aforementioned desirable properties that are important to sensing applications, including gas permeability, adhesion to aqueous-based organic polymer matrices, low temperature processing, and the like. The applicability of such mixtures and materials in a photolithographic process for the manufacture of microfabricated sensors has not previously been considered.

Indeed, the inventors of the present invention have found that polymeric materials having the sesqui form $(RSiO_{3/2})_x$ $(R'SiO_{3/2})_y$, where R comprises an organic moiety (e.g., alkyl, alkenyl, alkoxy and alkenoxy), and R' comprises an organic moiety or a hydrogen atom, are suitable for the practice of the present invention. Such mixtures and materials include Dow Corning resin WL-7154 (CAS number 609768-46-9) that is a polysiloxane in a solution of propylene glycol monomethyl ether acetate (PGMEA, CAS 108-65-6), with approximately 30% solids in mesitylene. The polysiloxane can be a 3-(methacryloxy) propylphenylsilsequioxane that is hydroxy-terminated. Such a polysiloxane solution is combined with a photoinitiator, such as, for example, phenylbis(2,4,6-trimethylbenzoyl)phosphine oxide (CAS number 162881-26-7), to provide the resin. When exposed to UV irradiation (e.g., wavelengths in the range of approximately 200 nm to approximately 400 nm), the methacryl groups on the polysiloxane are cross-linked by the action of the photoinitiator. Another Dow Corning resin, WL-5351, can also be used, with the resulting photoformed membranes exhibiting good gas permeability and flexibility.

Representative methods for obtaining these resins are described in, for example, U.S. Pat. No. 6,737,117, the entire contents of which are incorporated by reference herein. According to an exemplary embodiment, the resin blend can comprise, for example: a.) about 0.1 solids wt % to about 50 solids wt % of an organosiloxane resin comprising the formula $(RSiO_{3/2})_x(R'SiO_{3/2})_y$, in which R can be selected from $C_4$-$C_{24}$ alkyl, $C_4$-$C_{24}$ alkenyl, $C_4$-$C_{24}$ alkoxy, $C_8$-$C_{24}$ alkenoxy, or $C_4$-$C_{24}$ substituted hydrocarbon; in which R' can be selected from —H, $C_1$-$C_4$ unsubstituted hydrocarbon, or $C_1$-$C_4$ substituted hydrocarbon; in which x can be from about 5 mole % to about 75 mole %; in which y can be from about 10 mole % to about 95 mole %; and in which x+y can be at least about 40 mole %; and b.) about 50 solids wt % to about 99.9 solids wt % of a resin comprising at least about 90 mole % of the formula $HSiO_{3/2}$. As used herein, the terms "alkyl," "alkenyl," "alkoxy," and "alkenoxy" include linear, branched, and cyclic structures. As further used herein, "substituted hydrocarbon" includes a structure comprising carbon, hydrogen, and at least one other atom that does not substantially react with the $HSiO_{3/2}$ resin. According to an exemplary embodiment, the other atom can be selected from oxygen, nitrogen, silicon, sulfur or the like.

The resin comprising at least about 90 mole % $HSiO_{3/2}$ units can be referred to herein as a hydrosilsesquioxane resin. Up to about 10 mole % of silicon atoms in the hydrosilsesquioxane resin can be present in structures other than $HSiO_{3/2}$, including, for example, $HOSiO_{3/2}$ and $H(HO)SiO_{2/2}$, among others known to those of ordinary skill in the art of the present invention.

Suitable alternative photoformable materials also having the sesqui form can include, for example, beta-substituted organosilsesquioxane polymers, where the substituent can be, for example, acetoxyethyl and hydroxyethyl. Other materials include, but are not limited to, UV-curable acrylate-modified silicone elastomers (e.g., manufactured by Gelest, Inc.) and epoxycyclohexyl-modified silicones (ZIPCONE™ U Series by Gelest, Inc.), preferably ZIPCONE™ UA, ZIPCONE™ UE and UMS-18, which are photo-labile siloxane polymers that undergo transformation to a $SiO_2$-rich film by photo-elimination of beta-substituted alkyl groups.

These organosilanes, as described in, for example, U.S. Pat. No. 6,770,726, the entire contents of which are incorporated by reference herein, can be characterized as having the general formula $R_nSiX_{(4-n)}$, where n is 1 or 2, with n being 1 according to an exemplary embodiment of the present invention. In the general formula, X represents a halogen selected from chlorine, bromine, fluorine, iodine, or an alkoxy group selected from methoxy (—$OCH_3$), ethoxy (—$OCH_2CH_3$), and propoxy (—$OCH_2CH_2CH_3$, —$OCH(CH_3)_2$) substituents. According to an exemplary embodiment, X in the general formula can be chlorine, bromine, methoxy or ethoxy. In the general formula, R can represent the beta-substituted alkyl group that is a beta-substituted ethyl or propyl group or other equivalent beta-substituted alkyl group, where the beta-substituent is selected from chlorine, bromine, fluorine, iodine, hydroxy (—OH), methoxy (—$OCH_3$), ethoxy (—$OCH_2CH_3$), or acetoxy (—$OCOCH_3$). The beta-substituted alkyl group can be a beta-substituted ethyl group.

For deposition, such polymers can be diluted in isopropanol or methoxypropanol. Both the Gelest and Dow Corning materials discussed previously were found to have suitable storage properties at ambient temperature.

According to an exemplary embodiment of the present invention, a commercial i-STAT (i-STAT Corporation, East Windsor, N.J.) reference sensor was microfabricated through the steps up to, but excluding, the steps when a non-photoformable siloxane-nonsiloxane copolymer (11, illustrated in FIG. 1(a)) would have been spun down and patterned using the protective cap (12, illustrated in FIG. 1(a)) process described above.

Figure 1C:
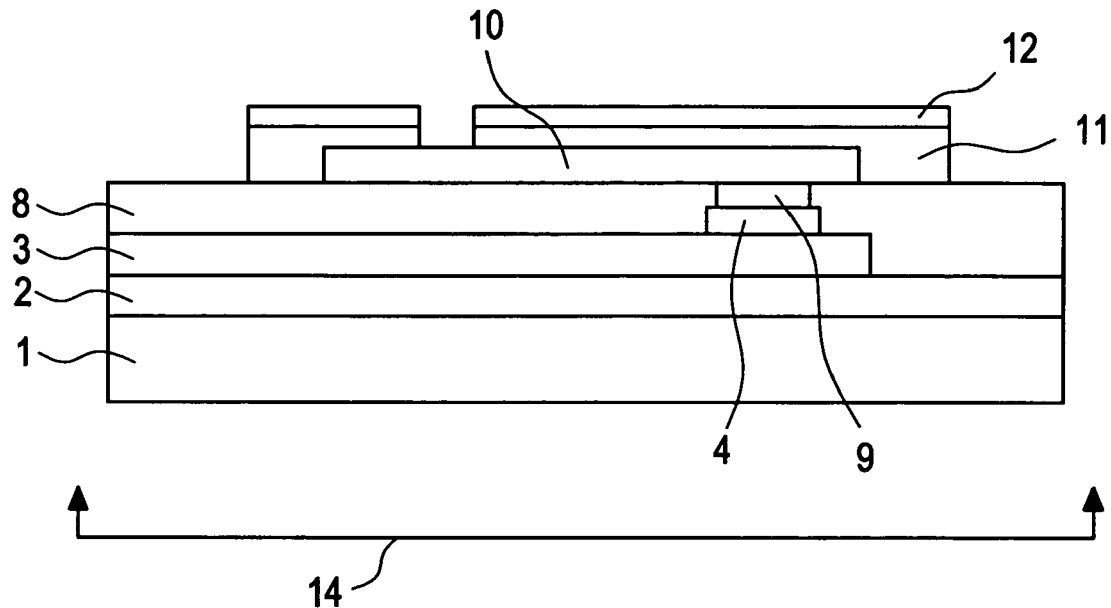
FIGS. 1(c) and 1(d) are diagrams illustrating elevation views of the reference sensor portion of the conventional device and the present device, respectively, in accordance with an exemplary embodiment of the present invention.
Figure 1D:
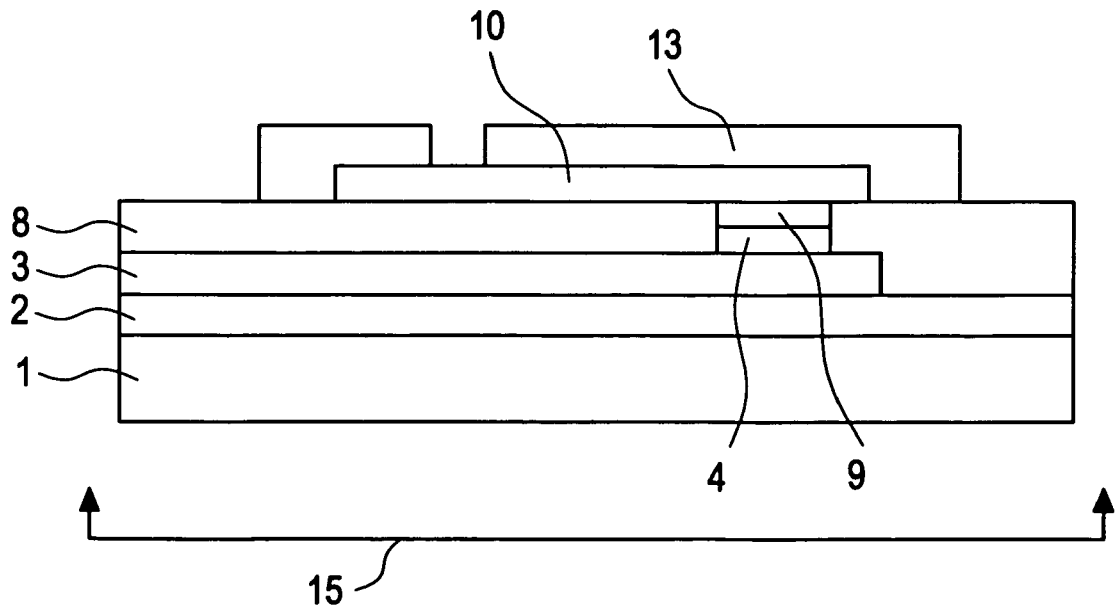

As illustrated in FIGS. 1(a), 1(b), 1(c) and 1(d), the microfabrication steps are as follows: a.) a silicon wafer (1) is thermally oxidized to form an insulating layer of silicon dioxide (2) on the wafer surface; and b.) a titanium-tungsten alloy (3) is sputtered onto the surface followed by a layer of silver (4). A conventional photoresist process, well known in the art (see, e.g., U.S. Pat. No. 5,200,051, the entire contents of which are incorporated by reference herein) is then used to pattern the metals to form the desired electrode (5), conductive line (6) and electrical contact pad (7), as illustrated in the plan view of FIG. 1(a) and the elevation view (14) of FIG. 1(c). A photoformable polyimide is then spun down onto the wafer and patterned to provide the desired passivation layer (8) covering the conductive lines. After chloridization (9) of the silver electrode, a layer of photoformable dichromated gelatin is spun down onto the wafer and patterned to provide an electrolyte support matrix layer (10) over the silver-silver chloride electrode and a surrounding area. It is noted that in FIGS. 1(a) and 1(b), the overall dimensions of the silicon wafer 1 are about 3 mm by about 5 mm. In addition, it is noted that the elevation views illustrated in FIGS. 1(c) and 1(d) are intended to show the relationship of the various layers, and are not to scale.

It is noted that electrodes can also be microfabricated using, for example, platinum, gold, iridium, other silver halides, carbon and the like, as is well known in the art. In addition to metal and non-metal electrodes, the sensing surface can also comprise, for example, a planar optical waveguide, evanescence wave sensor, surface acoustic wave sensor or the like. Such devices are well known in the art and are amenable to the matrix and membrane processes described herein.

In the improved process according to exemplary embodiments of the present invention, wafers manufactured as described above can be spin-coated with the Dow Corning resin WL-7154 (CAS number 609768-46-9) described above, using about 3-5 mL per wafer, spreading the material for about 10 seconds at a spin speed of approximately 900 RPM. Such a step was immediately followed by spinning at a higher speed of about 2000 RPM, for approximately 40 seconds, to achieve a membrane thickness of about 1.85 μm. Such a step was followed by a pre-exposure soft bake for about 60 seconds at approximately 100° C., featuring a gradual temperature step-down so as to improve adhesion and to prevent voids in the film due to entrapment of out-gassing solvents.

Next, a broadband spectrum U exposure of approximately 1000 mJ/cm$^2$ was performed through a photomask. The next step was an approximately 60 second bake at about 100° C., followed by an ambient cure for at least 30 minutes. The development step was performed on a wafer track by applying a spray of mesitylene for approximately 15 seconds, followed by an approximately 10 second isopropanol rinse at about 500 RPM, and then an approximately 20 second spin dry at about 3500 RPM. These steps yielded a rectangular patterned membrane layer (13) of dimensions of approximately 770×930 μm with a thickness of about 1.85 μm, as illustrated in the plan view of FIG. 1(b) and the elevation view (15) of FIG. 1(d).

As illustrated in FIG. 1(b), the membrane (13) can be patterned to provide any desired fixed geometric relationship with the underlying matrix, electrodes and other features on a surface, by judicious use of photomask alignment and exposure to realize such an objective. It is noted that this process can optionally include an initial spin-coating of an adhesion primer of about 2-4% methacryloxypropyltrimethoxysilane (CAS 4369-14-6) in propylene glycol monomethyl ether acetate (PGMEA). Such a primer can be used to enhance the adhesion of the resulting membrane to the surface. According to an exemplary embodiment, such use is not required, thereby simplifying the process and minimizing wafer exposure to additional chemicals.

Figure 2A:
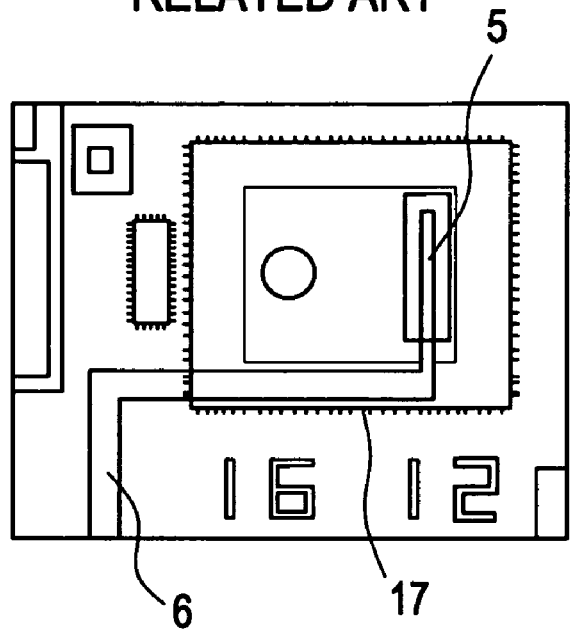
FIGS. 2(a) and 2(b) are diagrams illustrating details of the conventional and the present reference sensor membrane manufacturing processes, respectively, in accordance with an exemplary embodiment of the present invention.
Figure 2B:
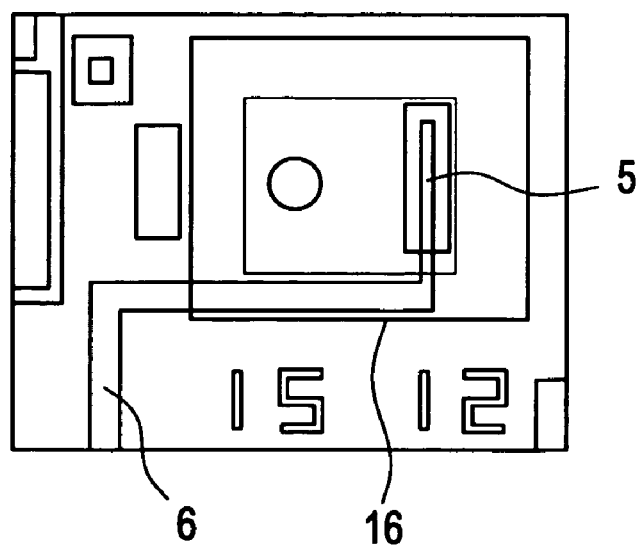

Those skilled in the art of the present invention will recognize that the present process is much simpler than the conventional process. Perhaps more importantly, the resin material patterns surprisingly well, as is illustrated in FIG. 2, which compares the conventional (FIG. 2(a)) with the present invention (FIG. 2(b)). Note that in FIG. 2(b), significant improvement in control of the edge of the pattern can be perceived, as exemplary embodiments of the present invention can provide a sharper and cleaner edge (16) compared to the conventional process (17).

The conventional process introduces lateral dimension variations due to an undercutting tendency in the etching process. Because the performance of a sensing device can depend on having a consistent path length from the edge of the membrane to the electrode, having a clearer, better defined edge reduces variability between sensors on the same wafer, and also between consecutively processed wafers, and between batches of wafers. Such an improvement is significant for this kind of device, where sensors are made in the millions and can be used in single-use analytical devices, such as the type sold by, for example, i-STAT Corp., as part of the I-STAT™ blood analysis system. Such a system is used to provide blood tests of analytes including, for example, glucose, oxygen, carbon dioxide, potassium and the like, in hospitals and elsewhere. Potentiometric sensors included in such a system require a reference sensor of the type described herein to operate.

The inventive process according to exemplary embodiments has additional desirable features. For example, the membrane layer has minimum tackiness after the track bake step, no equipment contamination is observed, and no damage to the film is observed after downstream processes, e.g., wafer dicing and sensor packaging. Most importantly, the material can be formulated to control thickness, both radially across a wafer containing several hundred individual sensors, and also from wafer-to-wafer, to within approximately 0.1 μm.

Control experiments demonstrated that if the membrane material is patterned so as to entirely or substantially entirely enclose the underlying matrix layer, there is no electrical contact (i.e., the electrode is open circuit) with respect to a second external test reference electrode structure upon contacting the device with an ionic aqueous solution. Such a test confirms that the membrane material, as patterned, is not conductive to ions, or more specifically that the rate of diffusion of ions is sufficiently slow as to become immeasurable during the time frame of the test, absent the intentional inclusion of openings which provide a salt bridge.

Where a second electrode is made on the above wafer structure of FIG. 1 (not shown) and also enclosed by the membrane, electrical contact can be established between these two electrodes when the membrane is contacted with an aqueous solution. Here, the previously dry-stored device wets-up as water vapor passes through the membrane and solvates the ions in the underlying matrix. Such a wet-up process takes about 10 to about 60 seconds for an approximately 1.85 μm membrane and was found to be dependent on thickness. Membranes in the range of about 0.1 μm to about 10 μm exhibited desirable wet-up properties. These experiments confirm that membranes, as processed using the inventive process according to exemplary embodiments, can be considered substantially ion-impermeable, but substantially gas permeable (e.g., water vapor).

In operation, the reference sensor serves to provide an essentially fixed or predictable half-cell potential against which the potential of a second sensor, e.g., a potassium electrode, can be measured. For example, in the i-STAT system, the reference sensor and other sensors, which are stored dry, are first contacted with an aqueous calibrant fluid with a known electrolyte composition. Such an initial contact allows for rapid wet-up of sensors (as described in, for example, U.S. Pat. Nos. 5,112,455 and 4,933,087, the entire contents of each of which are incorporated by reference herein), where water vapor passes though the gas-permeable membrane to solvate the underlying matrix containing chloride ions. These ions establish a predictable potential at the silver-silver chloride electrode. At the perimeter of the gas permeable membrane, the underlying matrix contacts the calibrant fluid and provides a liquid junction (or salt bridge) across which ions can flow to establish electrical continuity with an adjacent sensor, e.g., a potassium electrode. According to an exemplary embodiment, the analysis cycle constitutes sensors having about one to about two minutes in contact with a calibrant fluid and then about one minute in contact with a blood sample. Note that on the timescale of the electrochemical measurement in this system, the concentration of ions in the reference sensor matrix is essentially constant, thus providing a reliable reference potential.

Figure 3:
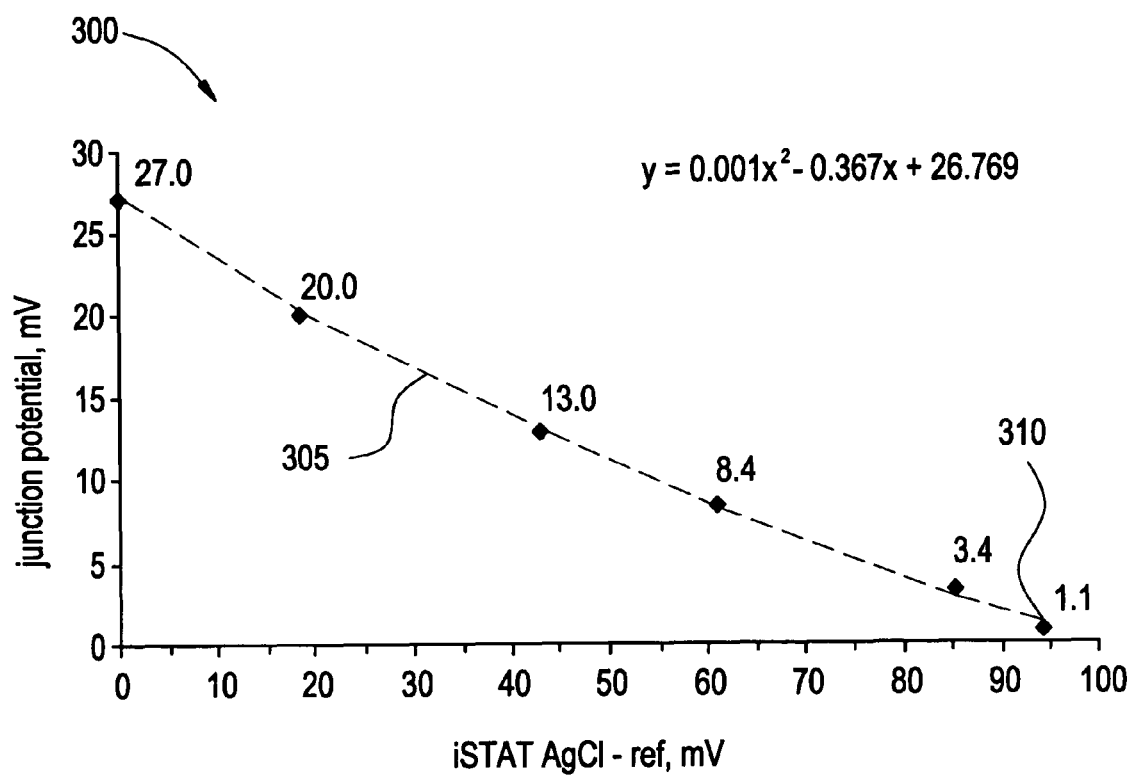
FIG. 3 is a graph illustrating the junction potential of the improved reference sensor as a function of the salt bridge KCl, in accordance with an exemplary embodiment of the present invention.

Regarding the actual performance of the improved reference sensor, an increase in the reference potential compared to ground is expected to reduce the magnitude of interferences from slow anions by reducing the liquid junction potential, according to the well-known Henderson relationship. FIG. 3 is a graph 300 illustrating the liquid junction potential 305 reaching a minimum 310 at a potential of approximately 100 mV. Such a potential can be increased by increasing the concentration of the aqueous KCl solution that is exposed to the wafer after patterning, as such a soak process will load more KCl salt into the reference sensor matrix layer. The improved gas permeable membrane using WL-7154 thus can be used to provide a reliable half-cell potential for potentiometic measurements.

The inventive gas-permeable membrane fabrication process according to exemplary embodiments has been applied to the manufacture of glucose sensors. Such sensors are also used in the i-STAT system. The process of manufacturing silicon wafers with arrays of glucose sensors is similar to that described for the reference sensor above (e.g., see U.S. Pat. Nos. 5,200,051 and 6,030,827, the entire contents of each of which are incorporated by reference herein), with the exception that the silver metal is replaced with platinum and the matrix is polyvinyl alcohol that also contains the enzyme glucose oxidase.

Figure 4:
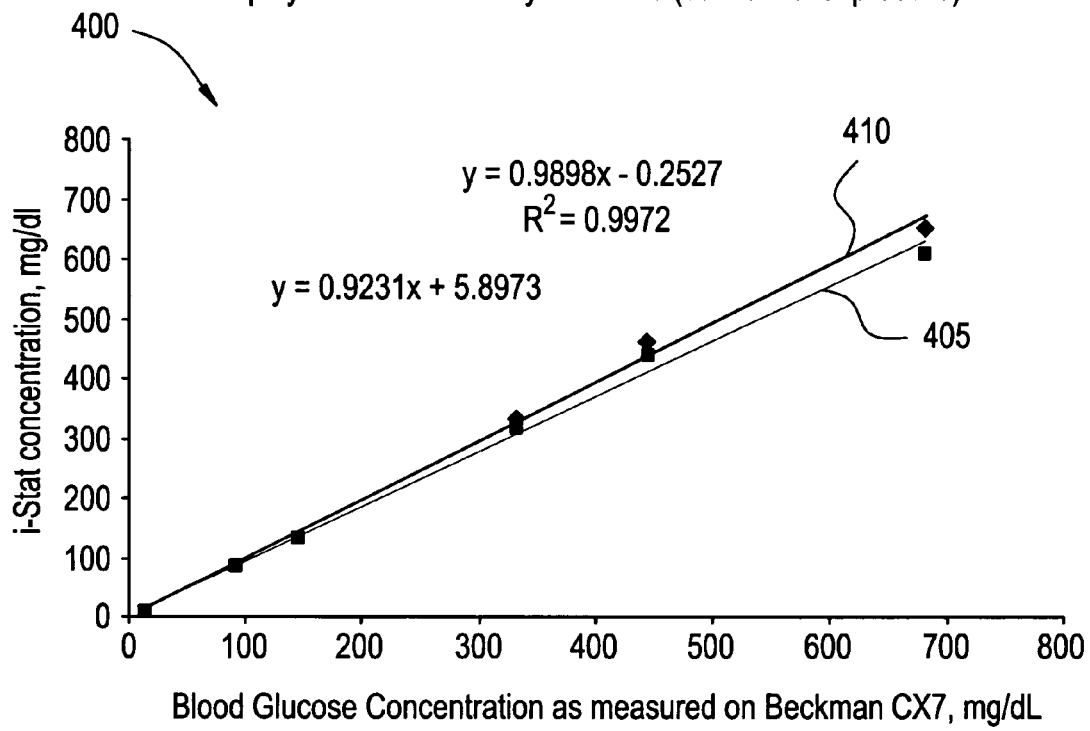
FIG. 4 is a graph illustrating the linear response of glucose sensors made according to the inventive process and the conventional process, respectively, as measured against a Beckman CX7 analyzer, in accordance with an exemplary embodiment of the present invention.

Deposition and patterning of the WL-7154 material was as described above for the reference sensor. In this example, oxygen that is required to support the enzymatic oxidation of glucose is supplied to the matrix by diffusing directly through the gas permeable membrane layer, whereas glucose only enters the matrix through one or more openings in the gas permeable layer. Such a process serves to ensure that the sensor output is linear over the entire range of glucose concentrations found in clinical diabetic blood samples. FIG. 4 is a graph 400 illustrating the satisfactory linear response over the range 10-680 mg/dL for both the new process 405 and the conventional process 410, as measured against a CX7 analyzer as the reference method. It has been found that this new gas-permeable process can also be applied to the manufacture of other amperometric sensors for other analytes including, for example, lactate and creatinine and the like.

Regarding the new glucose sensor, control experiments demonstrated that if the membrane material is patterned so as to entirely or substantially entirely enclose the underlying matrix layer containing glucose oxidase, along with an internal reference electrode, there is no glucose-dependent signal when contacted with various solutions containing different glucose concentrations. Such a test confirms that the membranes, as processed here, are essentially impermeable to non-gaseous molecules such as glucose, i.e., the rate of diffusion of glucose through the membrane is negligible compared to the rate of diffusion of oxygen and water vapor. Additional experiments showed that the rate of diffusion through the membrane of lactate, creatinine, creatine, ascorbate, urate and bilirubin, as well as ions including chloride, potassium, sodium, calcium, protons and hydroxide are all negligible. Such a finding is consistent with the membrane being substantially gas-permeable, but substantially impermeable to non-gaseous molecules and ions It is noted that the glucose oxidase in the above exemplary embodiment can be replaced by other bioactive molecules that confer specificity on a sensor. Such bioactive molecules include enzymes such as, for example, ascorbate oxidase, lactate oxidase, bilirubin oxidase, sarcosine oxidase, creatinase, creatininase, carbonic anhydrase and the like.

The improved gas-permeable membrane process according to exemplary embodiments has also been applied to the manufacture of oxygen ($pO_2$), carbon dioxide ($pCO_2$) and lactate sensors. Such sensors are also used in the i-STAT system. The process of manufacturing oxygen sensors on silicon wafers is similar to that described for the glucose sensor above (e.g., see U.S. Pat. No. 5,514,253, the entire contents of which are incorporated by reference herein) with the exception that the platinum metal is replaced with a microarray of gold electrodes, with a diameter of approximately 10 µm, and the polyvinyl alcohol matrix contains no enzyme, but optionally includes an inactive protein (e.g., albumin) to aid adhesion. Deposition and patterning of the WL-7154 material was as described above for the reference sensor.

Figure 5:
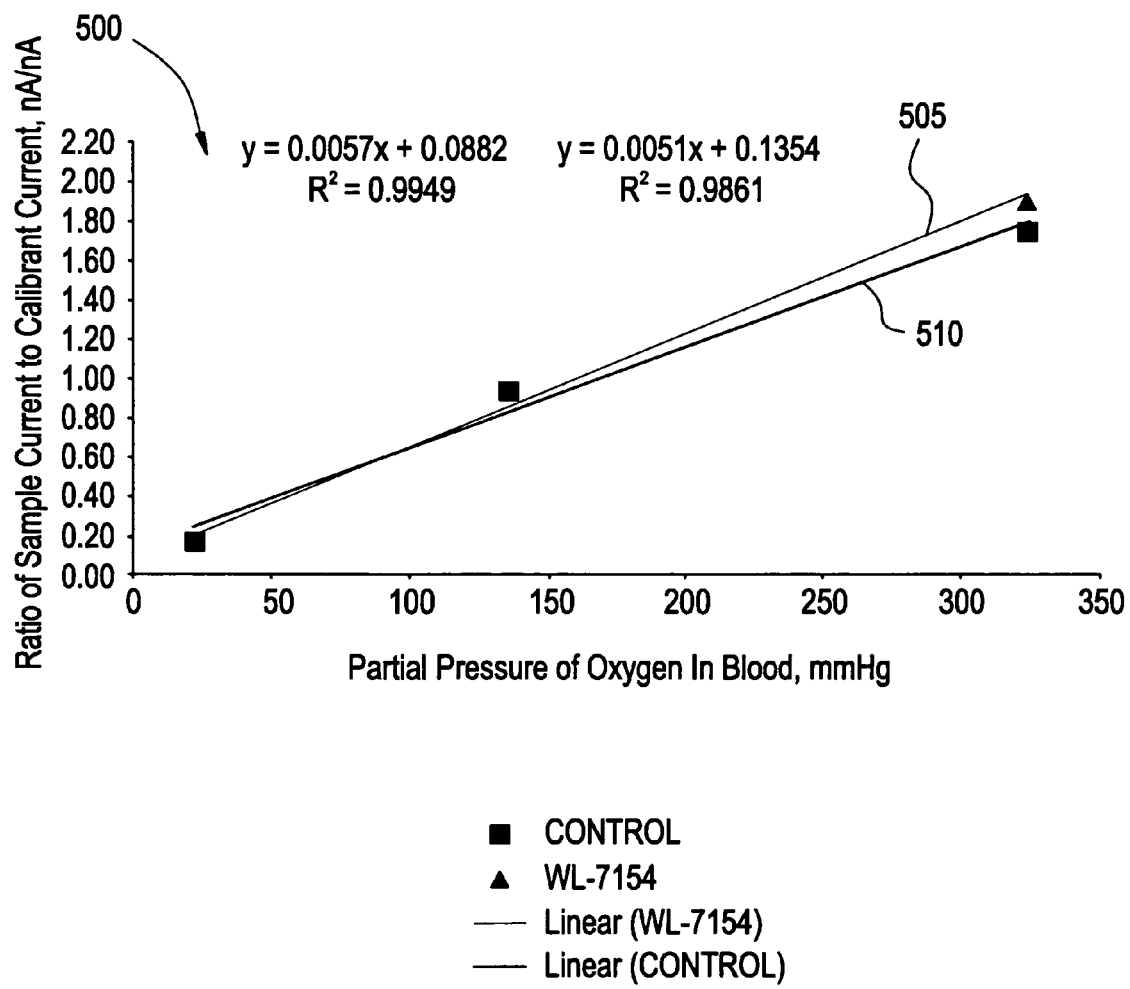
FIG. 5 is a graph illustrating the linear response of oxygen sensors made with the inventive process and the conventional process, respectively, as measured against the ABL blood gas analyzer, in accordance with an exemplary embodiment of the present invention.

FIG. 5 is a graph 500 illustrating that the oxygen sensor processed with the new material has a linear response 505 over a $pO_2$ range of 22-324 mm Hg and compares satisfactorily with the conventional process 510. It is noted that the ratio of sample current to calibrant current is proportional to $pO_2$ and can be converted from units of nanoamps (nA) to mm Hg using a suitable linear equation. Similar data were obtained for lactate sensors using the present and conventional processes 605 and 610, respectively, as illustrated in the graph 600 shown in FIG. 6. As can be seen in, for example, FIG. 6, the present process according to exemplary embodiments again provides suitable linearity.

The process of manufacturing carbon dioxide sensors on silicon wafers is similar to that described for the oxygen sensor above (e.g., see U.S. Pat. No. 5,514,253, the entire contents of which are incorporated by reference herein), with the exception that the matrix includes quinhydrone and the enzyme carbonic anhydrase. Quinhydrone serves to establish a redox potential that is a function of the proton concentration in accordance with the equilibrium between dissolved carbon dioxide, carbonic acid and bicarbonate and hydrogen ions. Carbonic anhydrase acts as a catalyst to this reaction. It is noted that alternative redox active species to quinhydrone can also be used, including, for example, ferrocene and substituted ferrocenes, and ferri- and ferrocyanide.

Deposition of the WL-7154 material for the pCO2 sensor can be as described above for the reference sensor. However, according to an exemplary embodiment, a carbon dioxide sensor can be manufactured by having the membrane material microdispensed in a volume of approximately 10 nL per sensor directly over the matrix layer and allowing it to dry to form a membrane layer enclosing or substantially enclosing the matrix. Flood exposure with UV radiation causes the membrane to be photo-developed and fixed. Such an approach avoids the need for spinning of the material, mask exposure and a development step, i.e., obviates patterning.

Both the oxygen and carbon dioxide sensors operate satisfactorily when the gas permeable membrane is formed so as to completely or substantially enclose the matrix layer, as long as a reference electrode is also present under the membrane. This is consistent with the polymer membrane being permeable to gaseous molecules such as oxygen and carbon dioxide.

In exemplary embodiments where the photoformable silsesquioxane material is deposited at specific locations on a surface by means of controlled microdispensing, teaching of the microdispensing process is described in, for example, U.S. Pat. No. 5,554,339, the entire contents of which are incorporated by reference herein.

According to a further alternative exemplary embodiment, where the sensor is a cylindrical device, e.g., a fiber optic element or wire electrode or the like, the sensor can be dip-coated with the photoformable copolymer and then flood exposed to UV radiation to establish the gas-permeable membrane.

According to further exemplary embodiments, in addition to forming the underlying matrix by patterning photoformable gelatin and polyvinyl alcohol, these matrices can also be formed onto a surface by microdispensing a desired volume of material followed by flood exposure to UV light. Alternatively, a matrix can be formed by microdispensing non-photoformable compositions such as, for example, gelatin, polyvinyl alcohol and nitrocellulose followed by a drying step.

The devices and methods according to exemplary embodiments of the present invention are suitable for microfabricated sensors to detect and measure metabolites, such as, for example, glucose and oxygen, and also as reference sensors, such as those based on silver-silver chloride or the like. Such sensors are suitable for making determinations in liquid samples including, for example, blood or the like, and are capable of being used for point-of-care diagnostics, including use at accident sites, in emergency rooms, in intensive care units, and the like, and also for non-medical purposes, such as environmental testing or the like.

It will be appreciated by those of ordinary skill in the art that the present invention can be embodied in various specific forms without departing from the spirit or essential characteristics thereof. The presently disclosed embodiments are considered in all respects to be illustrative and not restrictive. The scope of the invention is indicated by the appended claims, rather than the foregoing description, and all changes that come within the meaning and range of equivalence thereof are intended to be embraced.

All United States patents and applications, foreign patents and applications, and publications discussed above are hereby incorporated by reference herein in their entireties.

What is claimed is:

1. A sensing device, comprising:
a sensing surface;
a matrix overlaying the sensing surface; and
a photoformed membrane overlaying at least a portion of the matrix,
wherein the photoformed membrane comprises a directly photoformed organosiloxane polymer comprising a silsesquioxane polymer that is substantially permeable to gaseous molecules and substantially impermeable to non-gaseous molecules and ions.

2. The sensing device of claim 1, wherein the organosiloxane polymer comprises a beta-substituted silsesquioxane polymer.

3. The sensing device of claim 1, wherein the organosiloxane polymer comprises a hydrosilsesquioxane polymer.

4. The sensing device of claim 1, wherein a bound moiety is displaced by exposure to light to form the photoformed membrane.

5. The sensing device of claim 4, wherein the light comprises one or more wavelengths falling in the range of about 200 nanometers to about 400 nanometers.

6. The sensing device of claim 1, wherein the organosiloxane polymer is crosslinked by the action of a photoinitiator.

7. The sensing device of claim 1, wherein the photoformed membrane completely encloses the matrix.

8. The sensing device of claim 1, wherein the photoformed membrane is patterned to provide a substantially fixed geometric relationship with the matrix.

9. The sensing device of claim 1, wherein the photoformed membrane is patterned to provide a substantially fixed geometric relationship with the matrix and the sensing surface.

10. The sensing device of claim 1, wherein the sensing device is configured to detect one of oxygen, carbon dioxide, and water vapor.

11. The sensing device of claim 1, wherein the sensing device is configured to detect at least one of glucose, lactate, creatinine, ascorbate, urate, and bilirubin.

12. The sensing device of claim 1, wherein the ions are selected from the group consisting of chloride, potassium, sodium, calcium, proton and hydroxide.

13. The sensing device of claim 1, wherein the sensing surface is selected from the group consisting of a metal electrode, a non-metal electrode and an optical wave guide.

14. The sensing device of claim 1, wherein the sensing surface is selected from the group consisting of platinum, gold, iridium, silver, silver halide, silver chloride and carbon.

15. The sensing device of claim 1, wherein the sensing surface is adapted for potentiometry or amperometry.

16. The sensing device of claim 1, wherein the matrix is selected from the group consisting of polyvinyl alcohol, photoformed polyvinyl alcohol, gelatin, photoformed gelatin and nitrocellulose.

17. The sensing device of claim 1, wherein the matrix includes a bioactive molecule.

18. The sensing device of claim 1, wherein the matrix includes a bioactive molecule selected from the group consisting of glucose oxidase, lactate oxidase, bilirubin oxidase, ascorbate oxidase, carbonic anhydrase, sarcosine oxidase, creatinase and creatininase.

19. The sensing device of claim 1, wherein the matrix includes a redox species.

20. The sensing device of claim 1, wherein the matrix includes a redox species selected form the group the group consisting of quinhydrone, a ferrocene, ferrocyanide and ferricyanide.

21. The sensing device of claim 1, wherein the matrix includes an ion species.

22. The sensing device of claim 1, wherein the matrix includes chloride ions.

23. A reference electrode, comprising:
a silver-silver chloride sensing surface;
a matrix containing chloride ions overlaying the sensing surface; and
a directly photoformed membrane overlaying at least a portion of the matrix,
wherein the photoformed membrane comprises an organosiloxane polymer comprising a silsesquioxane polymer that is substantially permeable to water vapor and substantially impermeable to ions, and
wherein the photoformed membrane comprises at least one orifice configured to permit exchange of ions.

24. The reference electrode of claim 23, wherein a bound moiety is displaced by exposure to light to form the photoformed membrane.

25. The reference electrode of claim 23, wherein the organosiloxane polymer is crosslinked by the action of a photoinitiator.

26. The reference electrode of claim 23, wherein the photoformed membrane substantially encloses the matrix.

27. The reference electrode of claim 23, wherein the photoformed membrane is patterned to provide a substantially fixed geometric relationship with the matrix.

28. The reference electrode of claim 23, wherein the photoformed membrane is patterned to provide a substantially fixed geometric relationship with the matrix and the sensing surface.

29. A method of making a sensing device having a photoformed, gas-permeable membrane that is substantially impermeable to non-gaseous molecules and ions, comprising the steps of:
a.) applying an organosiloxane polymer comprising a silsesquioxane polymer having a bound labile moiety to a matrix overlaying a sensing surface to form a layer;
b.) applying ultraviolet (UV) radiation to at least a portion of the layer to remove the labile moiety and to cause the organosiloxane polymer comprising a silsesquioxane polymer to form an adhered membrane overlaying at least a portion of the matrix; and c.) exposing the layer to a developer to selectively remove the organosiloxane polymer comprising a silsesquioxane polymer not exposed to the UV radiation.

30. A method of making a sensing device having a photoformed, gas-permeable membrane that is substantially impermeable to non-gaseous molecules and ions, comprising the steps of:

a.) applying a silsesquioxane polymer to a matrix overlaying a sensing surface to form a layer;

b.) applying ultraviolet (UV) radiation to at least a portion of the layer to cause the silsesquioxane polymer to form an adhered membrane overlaying at least a portion of the matrix; and c.) exposing the layer to a developer to selectively remove the silsesquioxane polymer not exposed to the UV radiation.

* * * * *